(12) United States Patent
Satou et al.

(10) Patent No.: US 6,849,057 B2
(45) Date of Patent: Feb. 1, 2005

(54) PRESSURE-SENSITIVE ADHESIVE TAPE FOR FIXING A JOINT PORTION AND METHOD OF USING THE SAME

(75) Inventors: Hideo Satou, Osaka (JP); Masayuki Konno, Osaka (JP); Kodo Kishida, Osaka (JP); Yoshitada Morikawa, Osaka (JP); Osamu Oohira, Osaka (JP); Seishi Suzuki, Osaka (JP); Yuichi Inoue, Osaka (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 10/140,253

(22) Filed: May 8, 2002

(65) Prior Publication Data

US 2003/0069530 A1 Apr. 10, 2003

(30) Foreign Application Priority Data

May 11, 2001 (JP) ...................................... 2001-141021
Dec. 21, 2001 (JP) .................................. 2001-008323 U

(51) Int. Cl.[7] ................................................ A61F 5/00
(52) U.S. Cl. ............................ 602/75; 602/54; 602/41; 602/62
(58) Field of Search ............................ 602/63–66, 75, 602/62, 60, 61, 79, 903, 41–59; 128/881, 882, 888, 889, 892

(56) References Cited

U.S. PATENT DOCUMENTS

| | | | | |
|---|---|---|---|---|
| 2,875,758 A | * | 3/1959 | Fuzak et al. .................. 602/58 |
| 3,888,244 A | * | 6/1975 | Lebold ........................... 602/4 |
| 3,971,374 A | * | 7/1976 | Wagner ......................... 602/58 |
| 3,989,041 A | * | 11/1976 | Davies .......................... 602/62 |
| 4,245,630 A | * | 1/1981 | Lloyd et al. ................. 604/358 |
| 4,539,255 A | * | 9/1985 | Sato et al. ................... 442/286 |
| 4,724,831 A | * | 2/1988 | Huntjens ..................... 602/26 |
| 4,734,320 A | * | 3/1988 | Ohira et al. ................. 428/40.1 |
| 4,748,975 A | * | 6/1988 | Yashima ....................... 602/60 |
| 5,116,675 A | * | 5/1992 | Nash-Morgan ............. 428/343 |
| 5,139,476 A | * | 8/1992 | Peters ........................... 602/26 |
| 5,417,647 A | * | 5/1995 | Down ........................... 602/26 |
| 5,538,500 A | * | 7/1996 | Peterson ...................... 602/48 |
| 5,711,312 A | * | 1/1998 | Staudinger ................. 128/845 |
| 5,728,058 A | * | 3/1998 | Ouellette et al. ............. 602/62 |
| 5,792,091 A | * | 8/1998 | Staudinger ................... 602/57 |
| 5,906,637 A | * | 5/1999 | Davis et al. ................ 607/108 |
| 5,947,917 A | * | 9/1999 | Carte et al. ................... 602/52 |
| 6,103,369 A | * | 8/2000 | Lucast et al. ............... 428/354 |
| 6,191,337 B1 | * | 2/2001 | Himmelsbach .............. 602/54 |
| 6,211,426 B1 | * | 4/2001 | Abrams ....................... 602/46 |
| 6,245,959 B1 | * | 6/2001 | Ohira et al. .................. 602/41 |
| 6,402,712 B1 | * | 6/2002 | Gauvry ........................ 602/26 |
| 6,447,470 B2 | * | 9/2002 | Bodenschatz et al. ........ 602/75 |
| 6,459,013 B1 | * | 10/2002 | Himmelsbach .............. 602/58 |
| 6,495,230 B1 | * | 12/2002 | do Canto .................. 428/41.8 |
| 6,506,957 B1 | * | 1/2003 | Himmelsbach et al. ....... 602/41 |
| 2001/0051782 A1 | * | 12/2001 | Kinoshita et al. | |
| 2002/0045043 A1 | * | 4/2002 | Kuniya et al. | |

FOREIGN PATENT DOCUMENTS

| | | |
|---|---|---|
| EP | 0 354 315 A1 | 2/1990 |
| JP | 09010249 * | 1/1997 |
| JP | 2002-88534 A | 3/2002 |

OTHER PUBLICATIONS

Patent Abstracts of Japan, vol. 1997, No. 5, May 30, 1997 (corresponds to JPA 9–10249).

* cited by examiner

*Primary Examiner*—Nicholas D. Lucchesi
*Assistant Examiner*—Huong Q. Pham
(74) *Attorney, Agent, or Firm*—Sughrue Mion, PLLC

(57) ABSTRACT

A pressure-sensitive adhesive tape for fixing a joint portion includes a support of a generally rectangular shape having a longer side and a shorter side and a pressure sensitive adhesive layer on one side of the support in at least a portion thereof. The support is provided with a non-adherent portion or a weakly adherent portion. The tape has a cut line extending from an end of the shorter side to near the non-adherent or weakly adherent portion.

19 Claims, 9 Drawing Sheets

PRESSURE-SENSITIVE ADHESIVE TAPE FOR FIXING A JOINT PORTION AND METHOD OF USING THE SAME

BACKGROUND OF THE INVENTION

1. Field of the Invention

The present invention relates to a pressure-sensitive adhesive tape for fixing a joint portion and to a method of using the same. More particularly, the invention relates to a pressure-sensitive adhesive tape for fixing a joint portion that can alleviate a pain caused in a joint portion of the body of a person due to aging or at the time of exercise when adhered to the joint portion to fix it and to a method of using such a pressure-sensitive adhesive tape.

2. Description of a Related Art

Heretofore, many people have been suffering from a pain on a joint portion of the body such as knee, elbow, or wrist. Since joint portions have much to do with the action of a human, a pain on this portion will often result in difficulty in physical actions in daily life. In particular, the pain in the knee joint will in many cases cause dysbasia (trouble in walking) to have the patient bedridden, thus giving rise to serious problems not only physically but also mentally to the patient. Various factors are involved in the mechanism of generating a pain in a joint portion. The factors include, for example, deformation and wearout of joint cartilage. In the advancement of these are involved a decrease in muscle force of the muscle around the joint portion due to aging, over-use of the muscle, obesity and so forth, which give a great influence particularly on the knee joints, which generally tend to be under load of the body weight. As described above, the pain on the knee join is a serious problem and as will be clear from the situation in which advancement of aging society in recent years, excessive exercise by health-oriented people, and an increase in the number of obese persons due to change of food life are observed, there is a trend toward increasing population of those with a pain on the knee joint or joints. For this reason, a countermeasure for the pain on the knee joint has been keenly demanded and various studies are now being made on the method of treating it.

Methods that have been used to alleviate such a pain on the joint portion include various methods, for example, pharmacotherapy such as oral administration of analgesic, muscle relaxant and the like and local injection, physical therapy, which achieves resolution and pain killing by means of laser beam, interfering wave, microwave or the like, surgical therapy such as osteotomy or artificial joint whole replacement operation and so forth. As another approach, a method of fixing a joint portion to alleviate the pain thereon has been known. The method of fixing a joint portion uses a special-purpose pressure-sensitive adhesive tape, which is easily available from a pharmacy, for example, so that it is an effective means for alleviating a pain on a joint portion at low cost and in an easy-to-use manner as compared with other methods including the above-mentioned pharmacotherapy, visiting a hospital, operation and the like. Further, a method of winding a pressure-sensitive adhesive tape around a joint portion or ligament to support, reinforce or press the site is useful in preventing disorders or as first aid when playing sports (hereinafter, "taping" is defined as a method of fixing a joint portion by using a pressure-sensitive adhesive tape). However, most people have no expert knowledge on taping and if they have got knowledge by referring to textbooks it is difficult to get the skill. Under present circumstances, people have to visit an osteophatic clinic to ask taping by an expert trainer. However, it is time-consuming and cumbersome for a person having an injured joint portion to take trouble to visit a clinic such as an osteophatic clinic.

If taping is practiced by a laymen, use of commercially available pressure-sensitive adhesive tapes may always be attended with a discomfort since generally such pressure-sensitive adhesive tapes have an adhesive applied to all over the surfaces thereof and give a sense of incompatibility at the internal site of the joint where it is highly sensitive to stimulation. In addition, since the adhesive layer contacts the internal site of the joint where spontaneous perspiration occurs most frequently so that a problem arises that the surface of the skin at this site will get stuffy and skin irritation occurs.

In consideration of the above-mentioned problems of conventional pressure-sensitive sheets for taping, an object of the present invention is to provide a pressure-sensitive adhesive tape for fixing a joint portion which is easy to operate by a person having no expert knowledge on taping and when applied to a target site causes no sense of incompatibility at the internal site of the joint and an reduce significantly skin irritation due to getting stuffy or the like. Another object of the present invention is to provide a method of using such a pressure-sensitive adhesive tape for fixing a joint portion.

SUMARRY OF THE INVENTION

Accordingly, the inventors have made extensive studies in order to achieve the above-mentioned objects and as a result they have found that provision of a cut line on a specified position of a pressure-sensitive adhesive tape enables a person having no expert knowledge on taping to wear a pressure-sensitive adhesive tape for taping and further that provision of a non-pressure-sensitive adhesive applied-portion at the part of the pressure-sensitive adhesive tape expected to contact the internal site of a joint when in use can reduce a sense of incompatibility upon bending and stretching motion after applying it or getting stuffy due to spontaneous perspiration in that site. Thus the present invention has been accomplished.

That is, the present invention provides a pressure-sensitive adhesive tape for fixing a joint portion, comprising a support having a longer side and a shorter side and a pressure-sensitive adhesive layer on one side of the support in at least a portion thereof, wherein the support is provided with a non-adherent portion or a weakly adherent portion, and wherein the tape has a cut line extending from an end of the shorter side to near the non-adherent or weakly adherent portion.

Here, the non-adherent portion may comprise a non-adherent member and the tape may comprise two supports each having a pressure-sensitive adhesive tape on one side thereof coupled through the non-adherent member, forming a rectangular shape having longer sides and shorter sides.

The tape may comprise a rectangular support having longer sides and shorter sides having a pressure-sensitive adhesive tape layer over entire surface of one side thereof, and a non-adherent portion comprising a non-adherent member laminated on the pressure-sensitive adhesive tape layer.

The tape may comprise a rectangular support having longer sides and shorter sides with a pressure-sensitive adhesive tape layer over surface of one side thereof, and a weakly adherent portion where pressure-sensitive adhesive is partially provided on the side of the pressure-sensitive adhesive tape layer.

The non-adherent portion may be a punched out area.

The tape may have an elongation of 30% or more in the longitudinal direction.

The tape may have one cut line of a length extending from the central portion of the shorter side to the non-adherent or weakly adherent portion.

The tape may have a tab portion having a predetermined configuration on the top of a portion of pressure-sensitive adhesive tape separated by the cut line.

The support may have a tensile strength of 10 N/19 mm-width or more and a 20% modulus of 0.5 to 8 N/19 mm-width.

The support may comprise a high twist fabric or a knitted fabric having elasticity in two dimensions, the knitted fabric being laminated on one side thereof with a polyurethane film having waterproofing property and permeability.

Here, the polyurethane film is ultrathin.

The support may comprise a high twist fabric or a knitted fabric having elasticity in two dimensions, one side of the high twist fabric or knitted fabric being subjected to water repellent treatment.

The non-adherent member comprises one member selected from the group consisting of woven fabric, non-woven fabric, knitted fabric, paper, and plastic sheet.

The tape is for application to a knee joint.

Here, the shorter side has a length of 5 to 15 cm and the longer side has a length of 35 to 55 cm.

Furthermore, the present invention provides a method of using a pressure-sensitive adhesive tape for fixing a joint portion, comprising applying the non-adherent or weakly adherent portion of the above-mentioned pressure-sensitive adhesive tape for fixing a joint portion to an inner side site of a joint portion, separating the tape along the cut line, winding the separated tape portions around an outer side site of the joint to fix the joint site.

Here, the size of longer and shorter sides and the like must be such that the fixing function of taping on the joint site can be exhibited sufficiently.

The above and other objects, effects, features and advantages of the present invention will become more apparent from the detailed description to follow taken in conjunction with the accompanying drawings.

DETAILED DESCRIPTION

Figure 1:
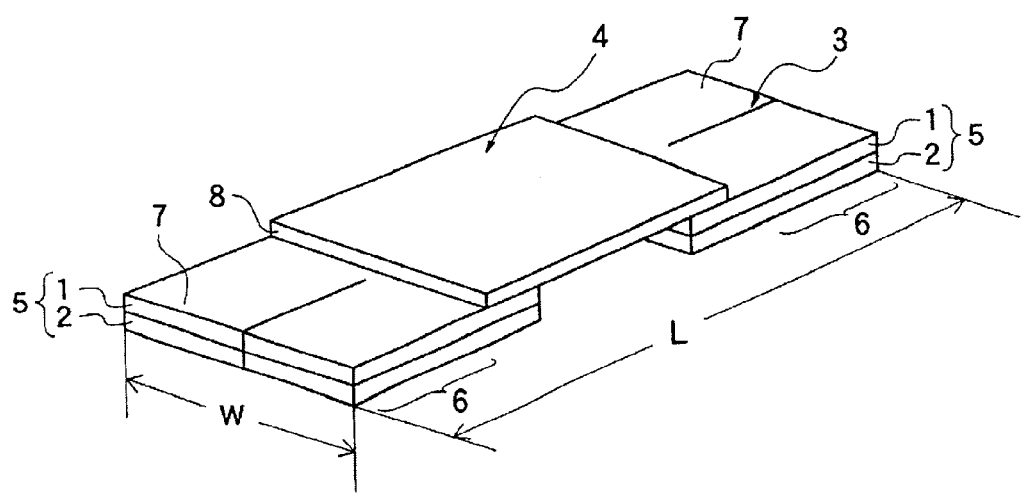
FIG. 1 is a perspective view showing the structure of a pressure-sensitive adhesive tape for fixing a joint portion according to a first embodiment of the present invention.

The pressure-sensitive adhesive tape of the present invention will be illustrated in detail with reference to the attached drawings. The same or like members are designated by the like reference numerals and explanation thereof will be omitted.

FIG. 1 is a perspective view showing the structure of a pressure-sensitive adhesive tape for fixing a joint portion according to a first embodiment of the present invention. The pressure-sensitive adhesive tape of the instant embodiment comprises a support having laminated on at least a portion thereof a pressure-sensitive adhesive tape layer (hereinafter, referred to as "tape element") and a non-adherent member, more particularly it comprises two such tape elements coupled to each other through the non-adherent member such that the non-adherent member bridges the two tape elements.

Figure 2A:
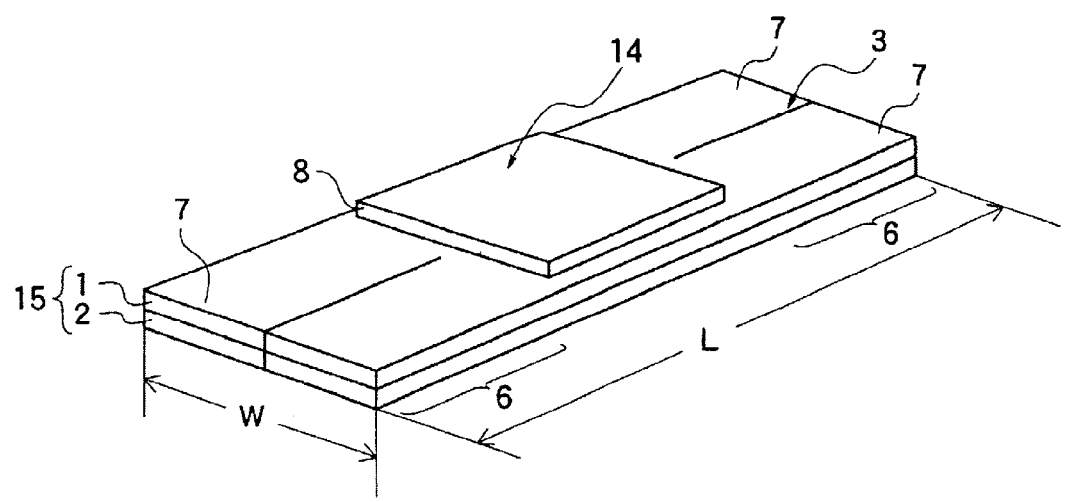
FIG. 2A is a perspective view showing the structure of a pressure-sensitive adhesive tape for fixing a joint portion according to a second embodiment of the present invention.
Figure 2B:
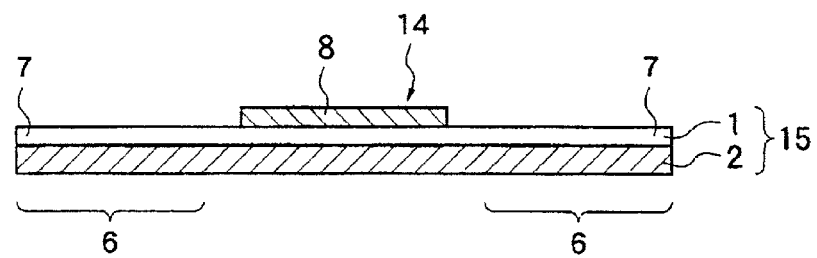
FIG. 2B is a front view of the tape shown in FIG. 2A.
Figure 3:
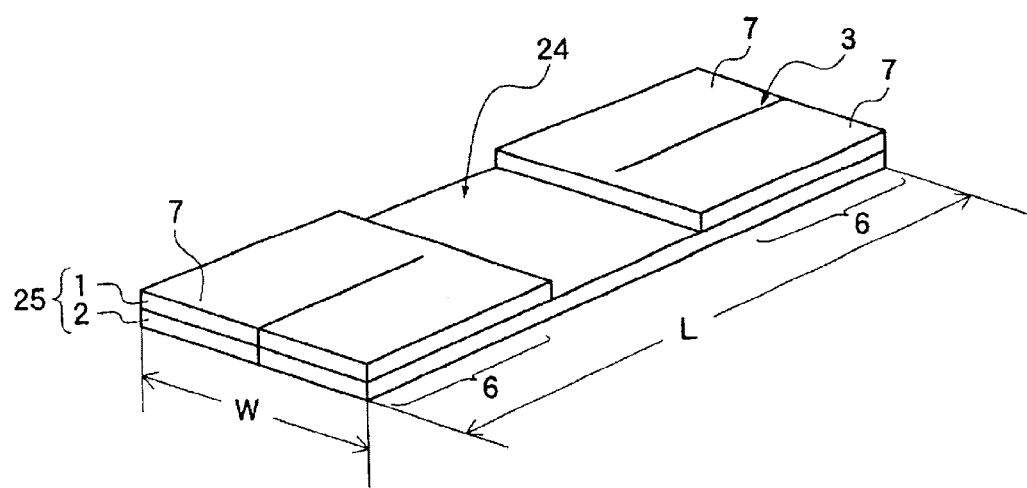
FIG. 3 is a perspective view showing the structure of a pressure-sensitive adhesive tape for fixing a joint portion according to a third embodiment of the present invention.

FIG. 2A is a perspective view showing the structure of a pressure-sensitive adhesive tape for fixing a joint portion according to a second embodiment of the present invention and FIG. 2B is a front view of the tape. In the embodiment shown in FIGS. 2A and 2B, the pressure-sensitive adhesive tape comprises one tape element and a non-adherent member and the non-adherent member covers a part of the pressure-sensitive adhesive tape layer on the tape element to form a non-adherent portion. FIG. 3 is a perspective view showing the structure of a pressure-sensitive adhesive tape for fixing a joint portion according to a third embodiment of the present invention. In the embodiment shown in FIG. 3, the pressure-sensitive adhesive tape comprises one tape element and an area where no pressure-sensitive adhesive tape layer is laminated is formed on a part of the pressure-sensitive adhesive tape layer to provide a non-adherent portion. In each of the Figures above, a reference numeral 1 designates a pressure-sensitive adhesive tape layer, 2 designates a support, 3 designates a cut line provided starting from an end (shorter end side) of the pressure-sensitive adhesive tape and longitudinally extending toward central portion thereof, 4 and 14 designate non-adherent portions formed with a non-adherent member 8, 24 designates a non-adherent portion formed by absence of lamination of a pressure-sensitive adhesive tape, 5, 15 and 25 designate tape elements having on at least a portion of the substrate laminated a pressure-sensitive adhesive tape layer, 6 designates an area of a tape element having a pressure-sensitive adhesive tape layer, corresponding to a pressure-sensitive adhesive tape portion to be wound around and attached to an adherend (e.g., knee joint portion), and 7 designates a tab portion on the top of the pressure-sensitive adhesive tape portion.

Figure 4A:
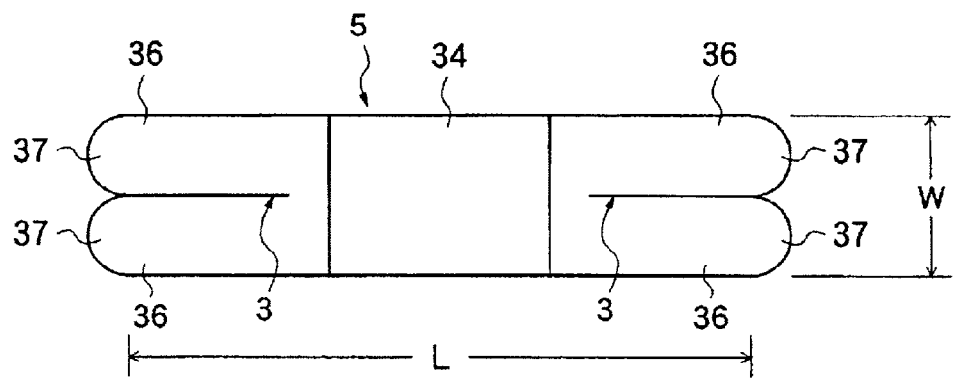
FIG. 4A is a plan view showing the structure of a pressure-sensitive adhesive tape for fixing a joint portion according to a fourth embodiment of the present invention.
Figure 4B:
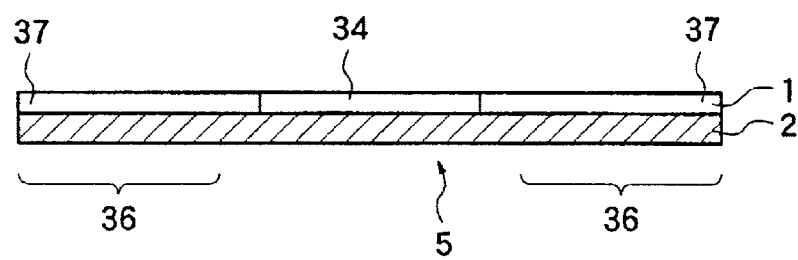
FIG. 4B is a front view of the tape shown in FIG. 4A.

In the present invention, instead of the non-adherent portion, a weakly adherent portion may be provided on a portion of the support. FIG. 4A is a plan view showing the structure of a pressure-sensitive adhesive tape for fixing a joint portion according to a fourth embodiment of the present invention and FIG. 4B is a front view of the tape shown in FIG. 4A. In the embodiment shown in FIGS. 4A and 4B, the pressure-sensitive adhesive tape comprises one tape element 5 and a weakly adherent portion 34 in place of the non-adherent portion is provided on the support 2. In this embodiment, a cut line 3 is provided on each end (shorter side end) starting substantially from a midpoint of the shorter side end extending toward the weakly adherent portion 34 to form pressure-sensitive adhesive tape portions 36. The separated portions 36 have each a tab portion 37 in the form of a semi-circle.

Figure 5:
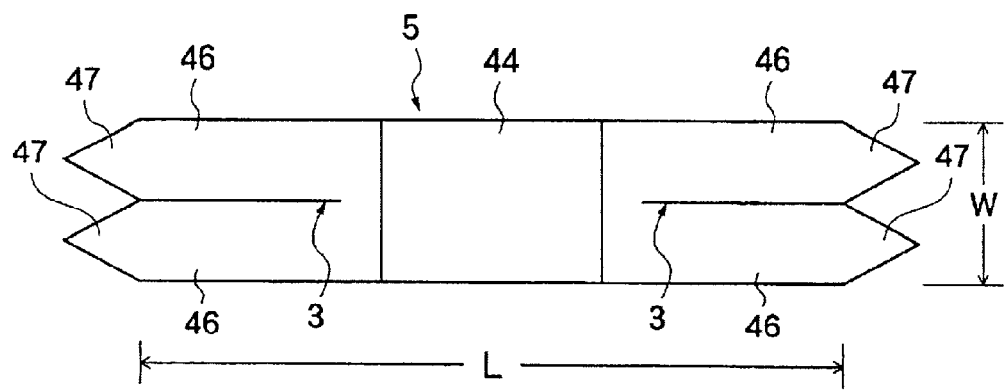
FIG. 5 is a plan view showing the structure of a pressure-sensitive adhesive tape for fixing a joint portion according to a fifth embodiment of the present invention.

FIG. 5 is a plan view showing the structure of a pressure-sensitive adhesive tape for fixing a joint portion according to a fifth embodiment of the present invention. In the embodiment shown, the pressure-sensitive adhesive tape portion 46 has a tab portion 47 substantially in the form of a triangle.

Figure 6:
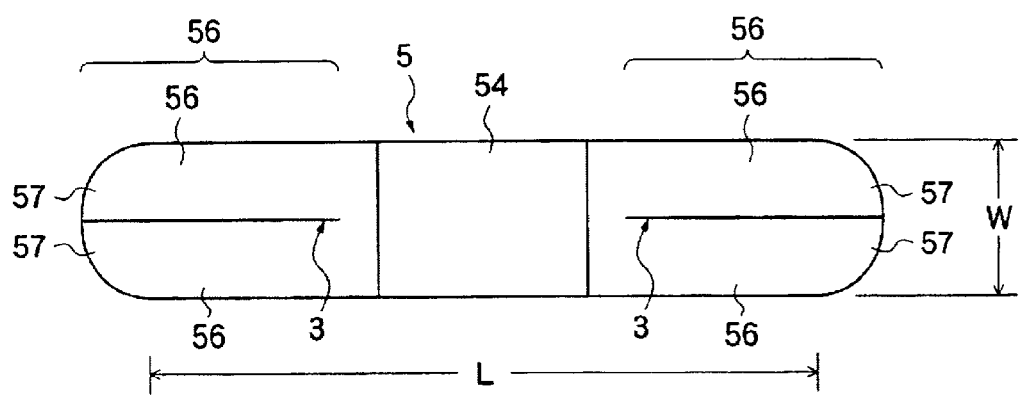
FIG. 6 is a plan view showing the structure of a pressure-sensitive adhesive tape for fixing a joint portion according to a sixth embodiment of the present invention.

FIG. 6 is a plan view showing the structure of a pressure-sensitive adhesive tape for fixing a joint portion according to a sixth embodiment of the present invention. In the embodiment shown, the tops of the pressure-sensitive adhesive tape portions 56 adjacent to each other side-by-side form a single larger semi-circle constituted by two adjacent tab portions 57.

Figure 7:
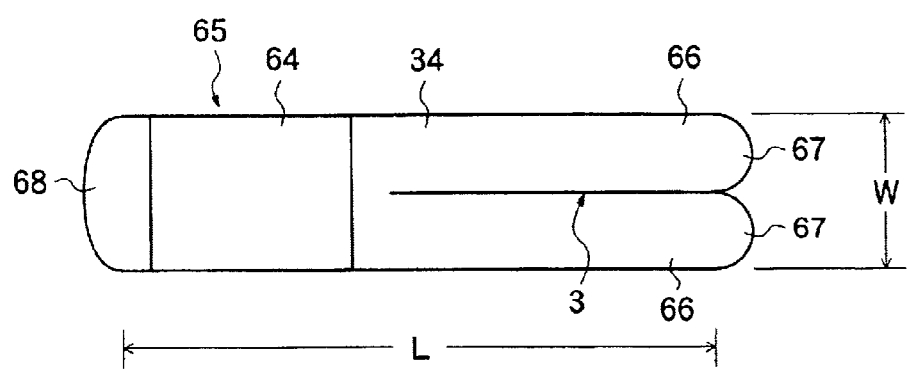
FIG. 7 is a plan view showing the structure of a pressure-sensitive adhesive tape for fixing a joint portion according to a seventh embodiment of the present invention.

FIG. 7 is a plan view showing the structure of a pressure-sensitive adhesive tape for fixing a joint portion according to a seventh embodiment of the present invention. In the embodiment shown, the pressure-sensitive adhesive tape portion is different in configuration of the tab portion of and length of the pressure-sensitive adhesive tape portion between the both ends (right and left ends in FIG. 7). The left-side tab portion 68 is of an oblong elliptic form and the two right-side tab portions 67 are each in the form of a smaller semi-circle. In addition, the length of the right-side pressure-sensitive adhesive tape portion is larger than that of the left-side pressure-sensitive adhesive tape portion. It is preferred that the cut line 3 is provided on each of both (right- and left-hand) sides. However, as in this embodiment, the cut line 3 may be provided in only one pressure-sensitive adhesive tape portion. In this case, a weakly adherent portion 64 is provided in a position somewhat biased from the center of the tape element 65; more particularly the cut line 3 is provided on the side of the longer pressure-sensitive adhesive tape portion. The pressure-sensitive adhesive tape having such a structure may be used by first winding the pressure-sensitive adhesive tape portion 68 having no cut line 3 around an outer side of a knee joint and then winding the pressure-sensitive adhesive tape portions 66 separated by the cut line 3 so as to surround the kneecap or patella.

Figure 2C:
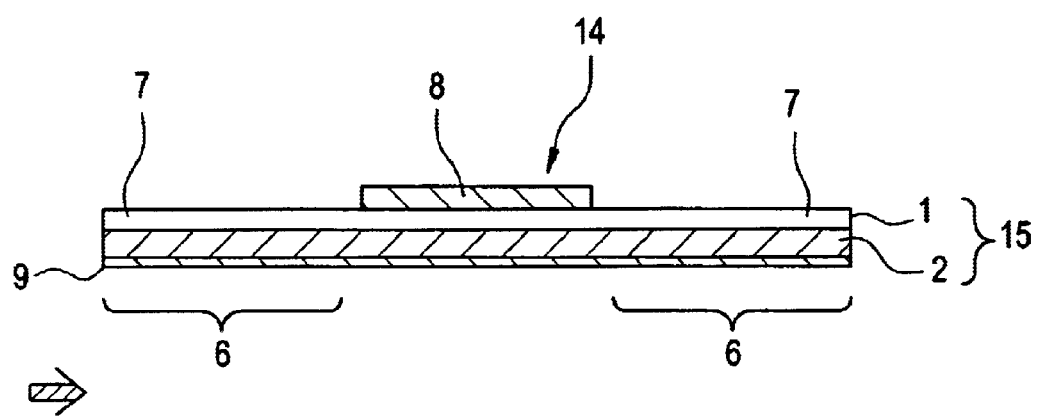
FIG. 2C is an illustration of a front view of another embodiment of the tape of FIG. 2A with an ultrathin plastic film 9, such as a polyurethane film, placed over the outer most layer, such as the back of a pressure sensitive adhesive tape over the substrate 2.

In the present invention, the non-adherent portion or weakly adhesive portion may be modified as appropriate in the pressure-sensitive adhesive for fixing a joint portion according to the embodiments shown in FIGS. 1 to 7, or the shape and structure of the pressure-sensitive adhesive tape portion and the like as shown in FIGS. 4 to 7 may be applied to the pressure-sensitive adhesive tape shown in FIGS. 1 to 3. Also, the non-adherent portion may be provided by punching a part of the tape.

The pressure-sensitive adhesive for fixing a joint portion of the present invention is a rectangular shape having longer sides (length: L) and shorter sides (length: W) so that it can be wound around a joint portion of human body. Here, the term "rectangular" shape refers to in addition to rectangles with corners at right angles, those having substantially rectangular shapes such as those with corners at an angle other than right angles or those having curved corners or those with ends having desired deformations, those having extensions on longer and/or shorter sides and so forth. The pressure-sensitive adhesive tape is adhered such that it can wrap inner and outer accessory ligaments of a joint such as the knee joint, elbow joint or the like. The pressure-sensitive adhesive tape has a non-adherent portion or a weakly adherent portion between the both ends thereof. The non-adherent portion is a portion that can be formed by use of a non-adherent member or can be a portion where no pressure-sensitive adhesive tape layer is laminated as described above while the weakly adherent portion can be a portion where is coated only on a part of the support as described hereinafter. These portions other than the adherent portions provides a domain on which the pressure-sensitive adhesive tape is attached to the inner side of bent portion of a joint such as a knee joint.

In the pressure-sensitive adhesive tape for fixing a joint portion according to the first embodiment of the present invention, the term "rectangular" shape refers to the whole structure having two tape elements coupled through the non-adherent member is "rectangular". Such a shape of the pressure-sensitive adhesive tape is not limited particularly as far as it can be wound around a joint portion of a human body as described above. Specifically, it is preferred that the pressure-sensitive adhesive tape of the present invention have a rectangular shape as shown in FIGS. 1 to 3 or oblong shape having extension on the shorter side as shown in FIGS. 4 to 7. Further, it is preferred that the length L of the longer side and the length W of the shorter side are determined as appropriate according to the size or other factors of the adherend portion (joint portion such as a knee joint or elbow joint). For example, when it is applied to a knee joint of an adult having a average habitus, the pressure-sensitive adhesive tape preferably has a size of L=35 to 55 cm and W=5 to 15 cm, more preferably L=40 to 50 cm and particularly preferably W=7 to 10 cm. The size and other factors may be selected in consideration of special habitus and the like.

When the pressure-sensitive adhesive tape is wound around a knee joint portion to substantially fixing the joint portion, if the length L of the longer side is smaller than 35 cm, there is a possibility that it cannot be wound around the knee joint portion sufficiently while the length L is greater than 55 cm, handleability will be deteriorate and there is a high possibility that the pressure-sensitive adhesive tape portion separated by the cut line 3 winds around the knee joint portion a whole round and further goes to the inner side of the bent portion of the joint portion so that the bending and stretching of the knee of the user will be restricted to some extent. If the shorter side is smaller than 5 cm, the pressure-sensitive adhesive tape cannot surround the knee-cap sufficiently while if it is greater than 15 cm, the pressure-sensitive adhesive tape also surrounds a portion remote from the kneecap, resulting in a decrease in fixability of the joint portion itself. Further, the pressure-sensitive adhesive tape of the present invention is provided with a cut line running from an end (shorter side) toward a central portion (non-adherent portion or weakly adherent portion) extending to near the central portion. The cult line impart the pressure-sensitive adhesive tape with effects of facilitating its attachment to a joint portion, which has been conventionally difficult, and of making taping operation easy. The number and place of cut lines is not limited particularly as far as a predetermined length of cut line is provided so that every one can practice taping easily. It is preferred that as shown in FIGS. 1 to 7, a cut line is provided on each and such that starting from each end starting from near midpoint of thereof extending to near the central portion of the tape.

The pressure-sensitive adhesive tape for fixing a joint portion of the present invention has pressure-sensitive adhesive tape portions 6, 36, 46, 56 and 66 separated by cut lines 3, each provided with a rectangular or non-rectangular tab portion. The tab portion is intended to increase visibility of the end of the pressure-sensitive adhesive tape. First the user recognizes the tab portion by the unaided eye, then feeling an end of the pressure-sensitive adhesive tape portion on the ventral surface of a digit and peels the tape by holding this portion. Since the tab portion contributes to fixability of the joint portion to a lesser extent, the shape of the tab portion may be freely selected in consideration of its design. However, from the viewpoint of functionality such as visibility or prevention of rolling up, or the like of the pressure-sensitive adhesive tape, the shape of the tab portion is preferably non-rectangular. For example, a semi-circular or semi-elliptic shape as shown in FIG. 4 and a substantially triangular shape as shown in FIG. 5 are preferred. The tab portion is provided preferably on each end of the pressure-sensitive adhesive tape portions separated by the cut line 3 as shown in FIG. 4. However, as shown in FIG. 6, adjacent two or more pressure-sensitive adhesive tape portions may have a single semi-circular end. In this case, such a tab may be formed as follows. First a semi-circular, semi-elliptic or substantially triangular extension is provided on one end of a rectangular pressure-sensitive adhesive tape and then a cut line 3 is provided in the end, for example, in the center thereof. The pressure-sensitive adhesive tapes having each a tab portion of semi-circular, semi-elliptic or substantially triangular extensions or having a tab portion of a semi-circular shape formed by two or more ends together are more difficultly peelable than a pressure-sensitive adhesive tape provided with a rectangular tab portion as shown in FIGS. 1 to 3 on the end thereof. The pressure-sensitive adhesive tapes with non-rectangular tabs are particularly effective for joint portions such as knee joints and the like where bending and stretching most frequently occur. The pressure-sensitive adhesive tapes on the both ends may have the same shape or different shapes from each other.

The pressure-sensitive adhesive tape of the present invention is attached so that the non-adherent portion provided on the side of the pressure-sensitive adhesive tape layer could contact an inner side site of a joint. Accordingly, when the pressure-sensitive adhesive tape of the present invention is worn, the pressure-sensitive adhesive tape layer does not directly contact the inner side site of the joint portion where the skin is sensible and much spontaneous perspiration occurs. This alleviates a sense of incompatibility felt at this site and at the same time skin irritation due to getting stuffy can be prevented. Furthermore, the non-adherent portion serves as a guide for indicating the right position of attaching the pressure-sensitive adhesive tape so that a user having no expert knowledge on taping can perform taping with ease.

The mode of forming the above-mentioned non-adherent portion includes, for example, a case where two tape elements are used as shown in FIG. 1, with the tape elements being coupled through a non-adherent member, a case where one tape element is used, with the non-adherent portion being a site in which a non-adherent member covers the pressure-sensitive adhesive tape layer as shown in FIGS. 2A and 2B, and a case where one tape element is used, with the non-adherent portion being a site in which pressure-sensitive adhesive tape layer is provided as shown in FIG. 3. Specific examples of the material of non-adherent member that can be used in the present invention include nonwoven fabrics, fabrics, knitted fabrics and the like made of polyester, rayon, nylon, polypropylene, polyethylene, polyurethane, cotton and the like. The shape of the non-adherent portion is not limited to a rectangular one as shown in FIGS. 1 to 3, but various forms such as trapezoid, polygonal and elliptic shapes may be used.

The support in pressure-sensitive adhesive tape for fixing a joint portion of the present invention is to support on one side thereof a pressure-sensitive adhesive tape layer and fixes a joint portion by means of its appropriate elongation to impart an effect of alleviating a pain on the joint portion. It is preferred that the support has an elongation of 30% or more in order to impart the pressure-sensitive adhesive tape with follow-up property and fixability with respect to a joint portion. The upper limit of the elongation of the support may be preferably 110% and more preferably 40 to 80% in consideration of fixability of a joint portion. Further, in the present invention, the pressure-sensitive adhesive tape including a support having a tensile strength of 10 N/19 mm-width or more, preferably 200 N/19 mm-width or less, in the longitudinal direction of the support and a 20% modulus of 0.5 to 8 N/19 mm-width is preferred. If the elongation increases, there is a possibility that the pressure-sensitive adhesive tape is disadvantageously fully stretched without recovery at the site where it is applied to the inner side site of the knee joint by repeated bending and stretching motion of the user. As the material for such a support, fabrics having elasticity, such as natural rubber sheet, synthetic rubber sheet, longitudinally stretching cloth including an elastic yarn as a warp (for example, spandex woven fabric including an elastic yarn comprising polyurethane in the core thereof), an elastic cloth including an elastic yarn for both warp and weft, hard twist fabric having incorporated a hard twist yarn, in the longitudinal direction, and a nit fabric being elastic in all directions, and laminate cloths comprising these woven fabric or knit fabric and polyurethane film may be used. As pressure-sensitive adhesive tape that can exhibit the effects of follow-up property, fixability, pressing property (kickback property) and the like, which are important for pressure-sensitive adhesive tape for taping, it is preferred to use a high twist fabric having the above-mentioned elongation and tensile strength. In the case where waterproofing property is additionally required, the above-mentioned woven fabric or knit fabric may be provided with a layer having both waterproofing property and permeability. For example, it is preferred to laminate an ultrathin plastic film thereon. Here, such fabrics having laminated thereon a polyurethane film having a thickness of about 5 to 30 μm is exemplified. Also, the materials for the support described above, for example, woven fabric, high twist fabric, knit fabric and the like, having subjected to water repellent treatment may be preferably used. The thickness of the support used in the present invention may be determined as appropriate depending on the site where the pressure-sensitive adhesive tape is used and the properties of the support used. In consideration of the follow-up property with respect to the skin, the thickness of the support is preferably 50 to 400 g/m$^2$ and more preferably 100 to 200 g/m$^2$ in the case where the use site is a knee.

On the other hand, for the pressure-sensitive adhesive used in the pressure-sensitive adhesive tape layer formed on one side of the above-mentioned support, various pressure-sensitive adhesives known or practically used in the field of pressure-sensitive adhesive tape for general taping may be used in the present invention. Specific examples of such conventional pressure-sensitive agents include acrylic based pressure-sensitive adhesive, rubber based pressure-sensitive adhesive, vinyl ether based pressure-sensitive adhesive, silicone based pressure-sensitive adhesive, gel based pressure-sensitive adhesive, and the like. In consideration of avoiding skin irritation and the like undesired effects, it is preferred to use acrylic based pressure-sensitive adhesive or gel based pressure-sensitive adhesive. The thickness of the pressure-sensitive adhesive layer may be selected as appropriate depending on the site where the pressure-sensitive adhesive tape is used and the kind of pressure-sensitive adhesive used as in the case of the support. It is preferably 20 to 400 μm and more preferably 40 to 120 μm in the case where the use site is a knee.

Concerning the coating of the pressure-sensitive adhesive, it may be coated either over the entire surface of one side or only a part thereof. The mode of coating may be selected as appropriate depending on the embodiment. In the case where a weakly adherent portion is formed, the pressure-sensitive adhesive is coated partially on one side of the support, for example, in a strip-like form in plural numbers. When a plurality of strip pressure-sensitive adhesive provided, it is preferred that a space serving as an air passage is secured between every adjacent two strips. In this case the form of air passage is not particularly limited and may be linear, undulation, partial grid or the like shape as far as flow of air therethrough is secured. Generally, undulation is preferred since it undergoes smallest possible a change in cross sectional area of the inter-strip space with a lapse of time. However, the shape of the air passage may be determined as appropriate depending on the properties of the pressure-sensitive adhesive used and the site where pressure-sensitive adhesive tape is used. Furthermore, when the pressure-sensitive adhesive is coated in the form of a strip, the inter-strip distance may be uniform. However, from the viewpoint of securing sufficient space on the inner side of the bent portion of a joint portion, the inter-strip distance in the weakly adherent portion may be set as large as possible. This results in prevention of getting stuffy on the skin portion where the pressure-sensitive adhesive tape is attached, in particular on the inner side site of the joint portion, which keeps the inner side of the joint portion in a comfortable state. The shape of the weakly adherent portion or non-adherent portion is not limited to the rectangular shape as shown in FIGS. 1 to 7 but may be of various other shapes such as trapezoidal, polygonal and elliptic shapes. Although in the configuration shown in FIGS. 1 and 3 to 7, the width of the weakly adherent or non-adherent portion is made identical with the length W of the shorter side, other configuration may be adopted; for example, as shown in FIG. 2, the width of the weakly adherent portion is made slightly smaller than the length W of the shorter side to provide an area where non-pressure-sensitive adhesive is coated on both edges of the support in the direction of width W.

Preferably, the pressure-sensitive adhesive tape of the present invention is covered on the surface of the pressure-sensitive adhesive layer with a separator (not shown) until it is used in order to prevent contamination of the surface of the pressure-sensitive adhesive layer. As the separator may be used any separator conventionally used for pressure-sensitive adhesive tapes and sheets intended to generally apply to the skin may be employed. Specifically, for example, wood free paper, glassine paper, parchment paper and the like or wood free paper or the like laminated with a polyethylene film, coated with a release agent having releasability, such as silicone, on the surface thereof, or a wood free paper or the like anchor coated with a resin, and so on may be used.

Figure 8:
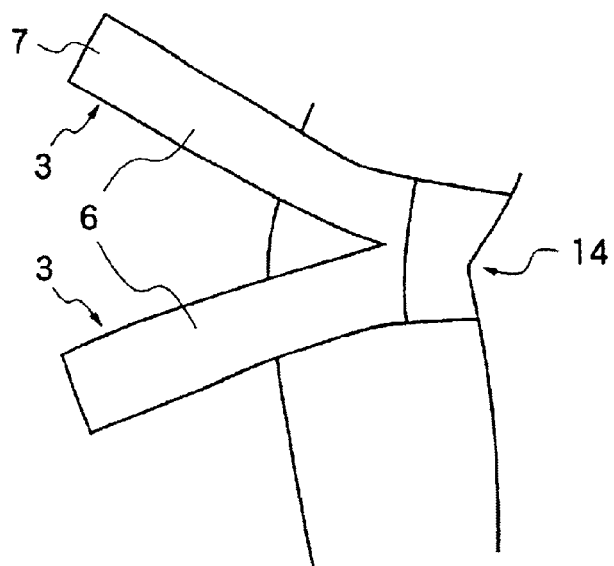
FIG. 8 is a side view illustrating the method of fixing a joint portion of a human body by using a pressure-sensitive adhesive tape for fixing a joint portion according to an embodiment of the present invention.
Figure 9:
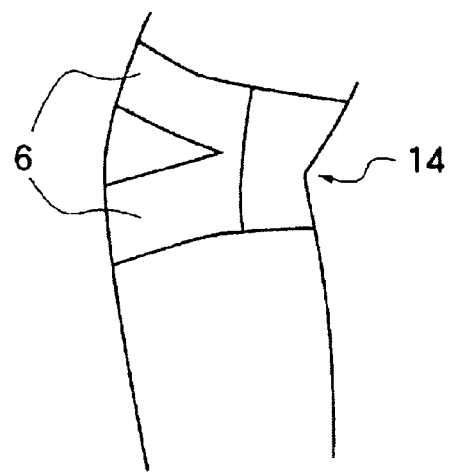
FIG. 9 is a side view illustrating the method of fixing a joint portion of a human body by using a pressure-sensitive adhesive tape for fixing a joint portion according to an embodiment of the present invention.
Figure 10:
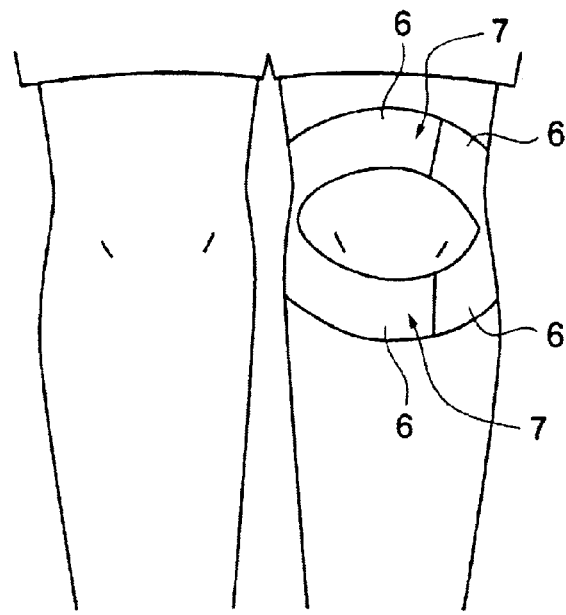
FIG. 10 is a front view illustrating the method of fixing a joint portion of a human body by using a pressure-sensitive adhesive tape for fixing a joint portion according to an embodiment of the present invention.
Figure 11:
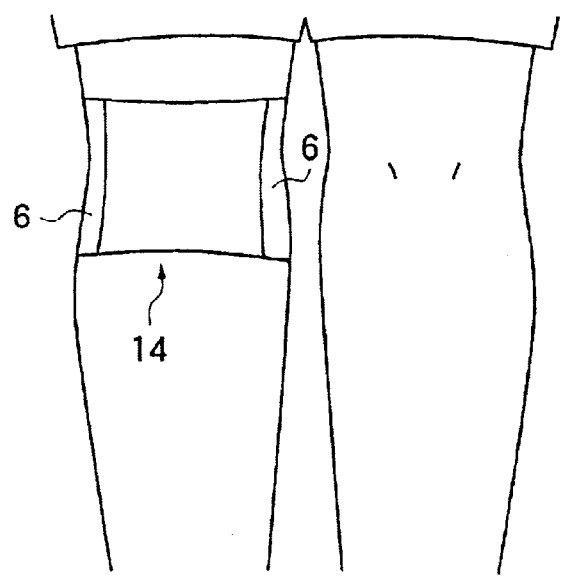
FIG. 11 is a rear view illustrating the method of fixing a joint portion of a human body by using a pressure-sensitive adhesive tape for fixing a joint portion according to another embodiment of the present invention.

Next, the method of using a pressure-sensitive adhesive tape of the present invention will be illustrated by referring to an example in which the tape is applied to a knee joint. FIGS. 8 to 11 are diagrams for illustrating a method of attaching the pressure-sensitive adhesive tape for fixing a joint portion according to the second embodiment of the present invention to the knee joint of the left leg of a human body. FIGS. 8 and 9 are side views, respectively, and FIG. 10 is a front view. FIG. 11 is a rear view. In each of FIGS. 8 to 11, reference numeral 6 designates a pressure-sensitive adhesive tape portion separated by the cut line 3.

In accordance with the method of using the pressure-sensitive adhesive tape of the present invention, first a non-adherent portion 14 is applied to an inner side site of a joint portion (a rear side site in the case of a knee joint portion) and one of pressure-sensitive adhesive tape portions 6 separated by the cut line 3 is wound around an outer side site of the joint portion (around the kneecap in the case of the knee joint). Then, the pressure-sensitive adhesive tape portion 6 on the other side is similarly wound around the outer side site of the joint portion. This makes it possible to apply the pressure-sensitive adhesive tape so that one of the pressure-sensitive adhesive tape portions 6 can be superposed on the other of the pressure-sensitive adhesive tape portions 6 in the front of the knee joint portion. FIG. 10 is an illustration of this state as seen from the front side and FIG. 11 is an illustration as seen from the rear side. This winding method can give rise to good fixability of the tape to the joint portion so that the pain in the joint portion of the user can be alleviated. The pressure-sensitive adhesive tape of the present invention featured by the existence of a non-adherent portion and of cut lines is distinct with respect to the position and method of application so that any person even having no expert knowledge on taping ca perform taping with ease.

Figure 12:
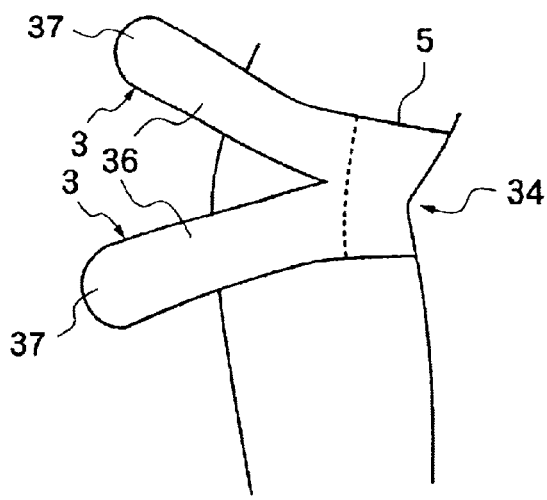
FIG. 12 is a side view illustrating the method of fixing a joint portion of a human body by using a pressure-sensitive adhesive tape for fixing a joint portion according to another embodiment of the present invention.
Figure 13:
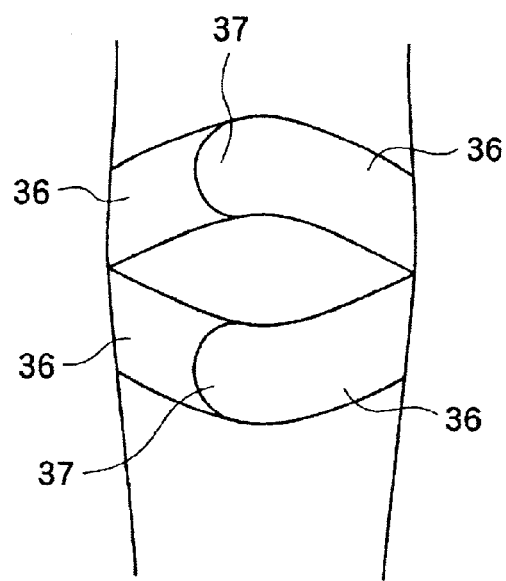
FIG. 13 is a front view illustrating the method of fixing a joint portion of a human body by using a pressure-sensitive adhesive tape for fixing a joint portion according to another embodiment of the present invention.

FIGS. 12 and 13 are diagrams for illustrating the method of attaching the pressure-sensitive adhesive tape for fixing a joint portion according to the fourth embodiment of the present invention to the knee joint portion of the left leg of a human body. FIG. 12 is a side view of the peripheral region of the knee joint where the pressure-sensitive adhesive tape according to the fourth embodiment is attached and FIG. 13 is a front view of the peripheral region of the knee joint as seen from the front.

The pressure-sensitive adhesive tape for fixing a joint portion of the present invention is wound around the kneecap of a knee joint as shown in FIG. 13 by applying the weakly adherent portion 34 to the inner side (rear side) of the knee joint as shown in FIG. 12 and applying the pressure-sensitive adhesive tape portions 36 separated by the cut line 3 to the knee joint portion so that they can overlap one on another while peeling a separator (not shown). Attachment of the pressure-sensitive adhesive tape in this manner gives rise to good fixability with respect to the joint portion so that the pain can be alleviated. The pressure-sensitive adhesive tape of the present invention featured by the existence of a non-adherent portion 34 and of cut lines 3 is distinct with respect to the position and method of application so that any person even having no expert knowledge on taping ca perform taping with ease.

Similarly, the pressure-sensitive adhesive tapes for fixing a joint portion according to other embodiments of the present invention can be used at a joint portion. The pressure-sensitive adhesive tapes of the present invention featured by the existence of a non-adherent portion and of cut lines are distinct with respect to the position and method of application so that any person even having no expert knowledge on taping ca perform taping with ease. In embodiments where the pressure-sensitive adhesive tape has a non-rectangular tab on each end of the separated pressure-sensitive adhesive tape for fixing around the periphery of the knee joint site, for example, kneecap, coming-off of the pressure-sensitive adhesive tape while it is being applied is reduced to a lesser level and the operability at the time of peeling it is increased. In particular, in the case a pressure-sensitive adhesive tape specially designed to have a specified size for a knee joint is applied to a knee joint portion, the handleability of the tape is excellent so that the knee joint portion can be properly fixed.

EXAMPLES

Hereinafter, the present invention will be illustrated in detail by referring to examples. However, the present invention should not be construed as being limited thereto and various modifications may be made within the spirit and scope of the present invention. In the following examples, the obtained pressure-sensitive adhesive tapes for fixing a joint portion are to be attached to a knee joint.

Example 1

This example relates to production of a pressure-sensitive adhesive tape of the present invention having two pressure-sensitive adhesive tape substrates coupled through a non-adherent member. First, a release liner (basis weight: 70 g/m$^2$) made of paper treated with silicone was coated with an acrylic based pressure-sensitive adhesive of a dry thickness of 80 µm and dried. On the obtained pressure-sensitive adhesive layer was applied a high twist fabric (basis weight: 150 g/m$^2$) as a support to form a laminate consisting of a support, pressure-sensitive adhesive layer and a release liner.

The above laminate was subjected to punching to obtain a workpiece (tape element) of a rectangular shape with a width of 75 mm and a length of 180 mm formed of a cut line in a central portion of one shorter side extending 120 mm in length starting therefrom, that is, having the shape indicated by reference numeral 5 in FIG. 1. Two such workpieces were provided and they were placed with the shorter ends on the sides where no cut line was formed facing each other. The end of the release liner on the side of the shorter side was temporarily peeled off to provide an overlap portion for linking in a width of 10 mm on the pressure-sensitive adhesive layer and the two workpieces were coupled end-to-end with polyester nonwoven fabric (basis weight: 40 g/m$^2$) having a width of 75 mm and a length of 110 mm to obtain a pressure-sensitive adhesive tape of the present invention having a width of 75 mm and a length of 450 mm of the shape shown in FIG. 1.

Example 2

This example relates to production of a pressure-sensitive adhesive tape having one support and a non-adherent portion formed by covering the pressure-sensitive adhesive layer with a non-adherent member. The laminate prepared in Example 1 above was subjected to punching to obtain a workpiece (tape element) of a rectangular shape with a width of 75 mm and a length of 450 mm formed of a cut line in a central portion of each shorter side extending 120 mm in length starting therefrom, that is, one having the shape indicated by reference numeral 15 in FIGS. 2A and 2B. The release liner was temporarily peeled off and a polyester nonwoven fabric (basis weight: 40 g/m$^2$) having a width of 75 mm and a length of 110 mm was applied to the central portion where no cut line was provided to obtain a pressure-sensitive adhesive tape of the present invention having a width of 75 mm and a length of 450 mm of the shape shown in FIGS. 2A and 2B.

Example 3

This example relates to production of a pressure-sensitive adhesive tape having one support and a non-adherent portion formed by providing no pressure-sensitive adhesive layer on the support. First, an acrylic based pressure-sensitive adhesive was coated on the same release liner as used in Example 1 to a dry thickness of 80 µm by alternately performing pattern coating in a width of 110 mm without the adhesive and in a width of 340 mm with the adhesive and then the coated support was dried. On the pressure-sensitive adhesive layer was applied the same high twist fabric as used in Example 1 as a support to form a laminate consisting of a support, pressure-sensitive adhesive layer and a release liner. The above laminate was subjected to punching to obtain a workpiece (tape element) having a width of 75 mm and a length of 450 mm of the shape shown in FIG. 3, having an adhesive pattern consisting of a first area with the adhesive in a length of 170 mm, a second area without the adhesive in a length of 110 mm and a third area with the adhesive in a length of 170 mm.

Example 4 (Comparative)

The laminate obtained in Example 1 was subjected to punching to obtain a workpiece having a width of 37.5 mm and a length of 450 mm, that is, one having a half the width of the workpiece of Example 1. The release liner of the work piece was peeled off and a polyester nonwoven fabric (having the same basis weight as Example 1) having a width of 37.5 mm and a length of 110 mm was applied to the central portion in the longitudinal direction to obtain a comparative pressure-sensitive adhesive tape of a rectangular shape having a width of 37.5 mm and a length of 450 mm in length, provided with a non-adherent member as a non-adherent portion on the side of the pressure-sensitive adhesive layer in the central portion in the longitudinal direction. Two such pressure-sensitive adhesive tapes were used in parallel to each other. That is, the two obtained pressure-sensitive adhesive tape were arranged in parallel to each other so that substantially no gap could be present between them and applied so that the non-adherent portions of the tapes could attach to the inner side site of the a knee joint portion and wound therearound so that substantially no gap could be present between the two tapes.

Example 5 (Comparative)

The workpiece (tape element) before applying a polyester nonwoven fabric thereto in Example 2 was used as a comparative pressure-sensitive adhesive tape.

The pressure-sensitive adhesive tapes obtained in Examples 1 to 5 were applied to knee joint portions of 20 volunteers of thirties or higher in age and their patch performance was evaluated according to the following criteria.

[Pain-alleviating Effect on a Knee Joint]

The pain-alleviating effect on a knee joint was evaluated according to four ratings of:

A: "The knee is very comfortable",
B: "Less pain on the knee",
C: "Feel light knee", and
D: "No change".

Table 1 shows the number of volunteers corresponding to each rating. The ratings of "the knee is very comfortable", "less pain on the knee", and "feeling light knee" were defined as effective to alleviation of the pain in the knee joint portion. Table 1 also shows the ratio of effective cases.

TABLE 1

|   | Example 1 | Example 2 | Example 3 | Example 4 (Comparative) | Example 5 (Comparative) |
|---|---|---|---|---|---|
| A | 5 | 7 | 6 | 1 | 0 |
| B | 5 | 3 | 4 | 4 | 0 |
| C | 5 | 5 | 5 | 1 | 1 |
| D | 5 | 4 | 4 | 14 | 19 |
| Ratio of effective cases | 0.7 | 0.75 | 0.75 | 0.3 | 0.05 |

[Feeling of Attachment]

The feeling of attachment of the pressure-sensitive adhesive tape was evaluated by the following four ratings of:

A: "very comfortable"
B: "no problem"
C: "uncomfortable"
D: "very uncomfortable".

Table 2 shows the number of volunteers corresponding to each rating. Of the above-mentioned ratings, "very comfortable" and "no problem" were defined as effective for giving good feeling of attachment. Table 2 also shows ratio of effective cases.

TABLE 2

|   | Example 1 | Example 2 | Example 3 | Example 4 (Comparative) | Example 5 (Comparative) |
|---|---|---|---|---|---|
| A | 15 | 13 | 9 | 12 | 0 |
| B | 5 | 7 | 10 | 6 | 7 |
| C | 0 | 0 | 1 | 1 | 11 |
| D | 0 | 0 | 0 | 1 | 2 |
| Ratio of effective cases | 1 | 1 | 0.95 | 0.9 | 0.3 |

[Operability]

The operability of the pressure-sensitive adhesive tape was evaluated by the following four ratings of:

A: "Easy to apply",
B: "No problem",
C: "Difficult to apply", and
D: "Very difficult to apply".

Table 3 shows the number of volunteers corresponding to each rating. Of the above-mentioned ratings, "easy to apply" and "no problem" were defined as effective for giving good operability. Table 3 also shows ratio of effective cases.

TABLE 3

|   | Example 1 | Example 2 | Example 3 | Example 4 (Comparative) | Example 5 (Comparative) |
|---|---|---|---|---|---|
| A | 6 | 8 | 7 | 2 | 7 |
| B | 12 | 10 | 11 | 5 | 9 |
| C | 2 | 2 | 2 | 10 | 4 |
| D | 0 | 0 | 0 | 3 | 0 |
| Ratio of effective cases | 0.9 | 0.9 | 0.9 | 0.35 | 0.8 |

As will be apparent from Tales 1 to 3 above, the pressure-sensitive adhesive tape of Examples 1 to 3 exhibited results superior to those of the pressure-sensitive adhesive tape of Examples 4 and 5 (comparative examples) in the effect of pain alleviation, feeling of attachment, and operability. Thus, the pressure-sensitive adhesive tapes showed differences in properties depending on their shape. Concerning Example 1, the high twist fabric could be effectively used in amounts smaller than those used in Examples 2 and 3. This is advantageous in that pressure-sensitive adhesive tapes can be produced at low costs. In addition the pressure-sensitive adhesive tape of Example 1 had good air permeability and gave no sense of incompatibility and was excellent in the effect of reducing getting stuffy on the inner side site of a knee joint. However, after attachment for a long time the nonwoven fabric was stretched or loosened to some extent so that the fixability with respect to the joint portion tended to decrease, resulting in a decrease in the pain-alleviating effect. As for Example 2, the nonwoven fabric was provided on the pressure-sensitive adhesive tape layer on the support, which caused the nonwoven fabric to contact inner side site of the joint portion more directly than in the case of pressure-sensitive adhesive tape obtained in Example 1 to give a softer touch to the skin, so that it tended to give excellent feeling of attachment. However, as compared with the pressure-sensitive adhesive tapes of Examples 1 and 3, the pressure-sensitive adhesive tape of Example 2 uses more expensive materials and incurs a higher cost. The pressure-sensitive adhesive tape of Example 3 is of a simple structure so that it can be produced easily. However, in this case, the high twist fabric directly contact the skin so that it tends to give a sense of incompatibility to the inner side site of the knee joint portion as compared with the pressure-sensitive adhesive tapes of Examples 1 and 2. As described above, it is revealed that the pressure-sensitive adhesive tape of Example 1 is featured by incurring low costs and excellent "getting stuffy" preventing effect, that of Example 2 is featured by excellent feeling of attachment, and that of Example 3 is featured by excellent productivity.

Example 6

A release liner (basis weight: 64 g/m$^2$) made of wood free paper having laminated thereon a polyethylene film, which in turn was treated with silicone was coated with an acrylic based pressure-sensitive adhesive of a dry thickness of 80 μm and dried. On the pressure-sensitive adhesive layer thus obtained was applied a high twist fabric (basis weight: 150 g/m$^2$, having a tensile strength of 160 N/19 mm-width in the longitudinal direction) as a support to form a laminate consisting of a support, pressure-sensitive adhesive layer and a release liner.

The above laminate was subjected to punching to obtain a workpiece (tape element) of a rectangular shape with a width (shorter side W) of 75 mm and a length (longer side L) of 450 mm formed of a cut line in a central portion of each shorter side extending 130 mm in length starting therefrom. Each end portion of the separated pressure-sensitive adhesive tape portions was further processed to provide a workpiece having a tab portion of an elliptic shape extending in the longitudinal direction in a length of 5 mm. This workpiece had a two-dimensional (planar) configuration shown in FIG. 4A. The release liner was temporarily peeled off and a polyester nonwoven fabric (basis weight: 40 g/m$^2$, SONTARA #8010 (registered trademark, produced by Toray DuPont Co., Ltd.) having a width of 75 mm and a length of 110 mm was applied to the central portion where no cut line was provided to obtain a pressure-sensitive adhesive tape for fixing a joint portion of the present invention having a width of 75 mm and a total length of 460 mm of the same profile as that shown in FIG. 2B. The release liner was provided with a back split on the non-adherent portion.

Example 7

A pressure-sensitive adhesive tape for fixing a joint portion having the planar shape shown in FIG. 4A was obtained in the same manner as in Example 6 except that the pressure-sensitive adhesive was partially coated in the form of a strip in plural numbers to form an adhesive pattern on the support in the area to be applied to the inner side site of a joint portion at a pitch of 5 mm for the coated portion and a pitch of 10 mm for non-coated portion.

Example 8 (Comparative)

A comparative pressure-sensitive adhesive tape for fixing a joint portion having a tab portion with a width of 75 mm and a total length of 460 mm was obtained in the same manner as in Example 6 except that no polyester nonwoven fabric was applied.

Example 9 (Comparative)

A comparative pressure-sensitive adhesive tape for fixing a joint portion having a tab portion with a width of 75 mm and a total length of 460 mm was obtained in the same manner as in Example 6 except that none of the shorter sides had a cut line in the central portion thereof.

Example 10 (Comparative)

A comparative pressure-sensitive adhesive tape was obtained in the same manner as in Example 6 excepting the following. That is, the laminate obtained in Example 6 was subjected to punching to obtain a workpiece (tape element) of a rectangular shape having a shorter side of 40 mm and a longer side of 450 mm with end portions being processed to form a tab portion extending in the longitudinal direction in a length of 5 mm. The release liner of the workpiece was temporarily peeled off and a polyester nonwoven fabric (basis weight: 40 g/m$^2$, SONTARA #8010 (registered trademark, produced by Toray DuPont Co., Ltd.)) having a width of 40 mm and a length of 110 mm was applied to the central portion where no cut line was provided. Two such pressure-sensitive adhesive tapes were wound around a knee joint portion so that no gap could be formed between the two tapes.

Example 11

The laminate prepared in Example 6 above was subjected to punching to obtain a workpiece (tape element) of a rectangular shape having a shorter side of 40 mm and a longer side of 340 mm with a cut line provided extending from each of the both end portions (shorter ends) thereof in a length of 80 mm and further with the end portions of the separated pressure-sensitive adhesive tape portions being processed to form a tab portion of an elliptic shape extending in the longitudinal direction in a length of 5 mm. Then, a pressure-sensitive adhesive tape for fixing a joint portion of the same profile as that shown in FIG. 2B having a width of 40 mm and a total length of 350 mm was obtained in the same manner as in Example 6 except that the release liner of the workpiece was temporarily peeled off and a polyester nonwoven fabric (basis weight: 40 g/m$^2$, SONTARA #8010 (registered trademark, produced by Toray DuPont Co., Ltd.)) having a width of 40 mm and a length of 110 mm was applied to the central portion where no cut line was provided.

Example 12

A pressure-sensitive adhesive tape for fixing a joint portion was obtained in the same manner as in Example 6 except that the laminate obtained in Example 6 was subjected to punching to form a rectangular workpiece (having no extension) having a shorter side of 160 mm and a longer side of 560 mm.

Example 13

A release liner (basis weight: 64 g/m$^2$) made of wood free paper having laminated thereon a polyethylene film, which in turn was treated with silicone was coated with an acrylic based pressure-sensitive adhesive of a dry thickness of 70 μm and dried to form a pressure-sensitive adhesive layer. On the other hand, on an elasticized knitted fabric smooth-knitted with polyester-made 75 denier yarn so as to have an elongation of 75% in the transverse direction and an elongation of 58% in the longitudinal direction was laminated a pressure-sensitive adhesive layer thus obtained was applied a polyurethane film having a thickness of 10 μm to form a support (basis weight: 114 g/m$^2$). The support had a tensile strength of 113 N/19 mm-width in the longitudinal direction. Then, the obtained support was applied to the formed pressure-sensitive adhesive layer to form a laminate consisting of a support, pressure-sensitive adhesive layer and a release liner in order.

The above laminate was subjected to punching to obtain a pressure-sensitive adhesive tape for fixing a joint portion having the planar configuration as shown in FIG. 4A.

[Effect of Alleviating a Pain on a Knee Joint]

The effect of alleviating a pain on a knee joint was evaluated by three ratings of:

A: "The knee is very comfortable",
B: "The pain on the knee slightly lessened", and
C: "No change".

Table 4 shows the results in terms of the number of volunteers corresponding to each rating.

TABLE 4

|   | Ex.6 | Ex.7 | Ex.8 | Ex.9 | Ex.10 | Ex.11 | Ex.12 | Ex.13 |
|---|------|------|------|------|-------|-------|-------|-------|
| A | 12   | 14   | 11   | 4    | 5     | 1     | 10    | 13    |
| B | 3    | 1    | 3    | 5    | 5     | 4     | 4     | 2     |
| C | 0    | 0    | 3    | 3    | 5     | 10    | 1     | 0     |

[Feeling of Attachment]

The feeling of attachment of the pressure-sensitive adhesive tape was evaluated by three ratings of:

A: "Very comfortable",
B: "No problem but a slight sense of incompatibility felt", and
C: "Very uncomfortable".

Table 5 shows the results in terms of the number of volunteers corresponding to each rating.

TABLE 5

|   | Ex.6 | Ex.7 | Ex.8 | Ex.9 | Ex.10 | Ex.11 | Ex.12 | Ex.13 |
|---|------|------|------|------|-------|-------|-------|-------|
| A | 15   | 13   | 2    | 3    | 7     | 12    | 1     | 14    |
| B | 0    | 2    | 3    | 4    | 6     | 2     | 3     | 1     |
| C | 0    | 0    | 10   | 9    | 2     | 1     | 11    | 0     |

[Pain When Peeling a Tape After Operation]

The pain when peeling a pressure-sensitive adhesive tape was evaluated by three ratings of:

A: "Can be peeled without problems",
B: "A slight pain felt", and
C: "A great pain felt".

Table 6 shows the results in terms of the number of volunteers corresponding to each rating.

TABLE 6

|   | Ex.6 | Ex.7 | Ex.8 | Ex.9 | Ex.10 | Ex.11 | Ex.12 | Ex.13 |
|---|------|------|------|------|-------|-------|-------|-------|
| A | 13   | 12   | 0    | 13   | 13    | 14    | 0     | 14    |
| B | 2    | 3    | 2    | 2    | 2     | 1     | 6     | 1     |
| C | 0    | 0    | 13   | 0    | 0     | 0     | 9     | 0     |

[Operability]

The operability of a pressure-sensitive adhesive tape was evaluated by three ratings of:

A: "Good for both attachability and peelability, the end portion being quickly recognizable",
B: "Slightly difficult to attach but good for peelability, the end portion being quickly recognizable", and
C: "Poor for both attachability and peelability, the end portion not being quickly recognizable."

Table 7 shows the results in terms of the number of volunteers corresponding to each rating.

TABLE 7

|   | Ex.6 | Ex.7 | Ex.8 | Ex.9 | Ex.10 | Ex.11 | Ex.12 | Ex.13 |
|---|------|------|------|------|-------|-------|-------|-------|
| A | 14   | 15   | 13   | 10   | 9     | 11    | 4     | 14    |
| B | 1    | 0    | 2    | 4    | 4     | 3     | 4     | 1     |
| C | 0    | 0    | 0    | 1    | 2     | 1     | 7     | 0     |

As will be apparent from Tables 4 to 7 above, the pressure-sensitive adhesive tape of Examples 6, 7 and 13 exhibited results superior to those of the pressure-sensitive adhesive tape of Examples 8 to 12 in the effect of pain alleviation, feeling of attachment, and operability. The pressure-sensitive adhesive tape of Example 7 was provided with a weakly adherent portion, which has an advantage in that the production process is simplified and the pressure-sensitive adhesive tape can be produced at low costs. The pressure-sensitive adhesive tape of Example 7 had good air permeability, gave no sense of incompatibility and had good less-getting-stuffy property in the area of the inner side of a knee joint. Furthermore, due to its pressure-sensitive adhesive tape being partially coated, it did not loosen during use. On the other hand, the pressure-sensitive adhesive tape of Example 6 gave good feeling of attachment because of nonwoven fabric being applied in the area where the pressure-sensitive adhesive tape contacts the inner side site of a knee joint. However, the situation was observed that it showed elongation of the nonwoven fabric to some extent after prolonged attachment.

Further, with the size of the pressure-sensitive adhesive tape of Examples 10 and 11, no sufficient effect of alleviation of the pain on the knee joint was obtained. In the case of pressure-sensitive adhesive tape obtained in Example 12, sufficient pain-alleviating effect was observed. However, the size of the whole article was rather too large to give easy handleability and the overlapped end portion was difficult to find. On the other hand, the end portion tended to roll up at corners. The pressure-sensitive adhesive tape of Example 8 was poor in feeling of attachment and caused a pain when it was peeled off. On the other hand, the pressure-sensitive adhesive tape of Example 9, which had no cut line, covered the kneecap, so that it did not exhibit the pain-alleviating effect.

[Water Resistant Self-back-adhesion]

(Water Resistant Self-back Adhesion Power)

On one side of a Bakelite (registered trademark, Union Carbide) plate of a size of 2 mm (thickness)×25 mm (width) ×ca. 150 mm (length) as an adherend was attached a 25 mm wide sample tape. On the backside of the sample tape was attached a sample tape by a conventional method and the samples were immersed in water at normal temperature (about 21 to 25° C.) for 30 minutes and then taken out. The samples were immediately measured of peel strength by a 180° peel method to obtain a peak value when peeled at a rate of 300 mm/minute. In this case, sample number (n) was n=3.

(Water Resistant Adhesion)

The pressure-sensitive adhesive tape for a joint portion of Examples 1 and 13 were attached on the knee joint portions of five volunteers of thirties in age in a state where the end portions were wrapped. The entire pressure-sensitive adhesive tape was wetted by pouring water thereto. In the wet state, the volunteers spent their daily life. After 5 hours, the state of peeling was observed with unaided eye. Evaluation was made in accordance with the following criteria. Table 8 shows the results obtained.

Criteria of Evaluation:
A: The wrapped portion in its entirety adhered after 5 hours.
B: The wrapped portion partially peeled off.
C: The wrapped portion mostly peeled off.

TABLE 8

|  |  | Pressure-sensitive adhesive tape of Example 1 | Pressure-sensitive adhesive tape of Example 13 |
|---|---|---|---|
| Water resistant self-back adhesion power (N/19 mm-width) |  | 0.65 | 2.95 |
| Water resistant adhesion power | A | 0 (Persons) | 5 (Persons) |
|  | B | 2 | 0 |
|  | C | 3 | 0 |

From Table 8, it can be seen that the pressure-sensitive adhesive tape for a joint portion of Example 1 had low water resistant self back adhesion power and the volunteers were in motion with the wrapped portion of the tape being in a wet state, after 5 hours, it revealed that none of them was successful in wearing the tape in a state where the wrapped portion thereof was entirely adhered to the knee joint portion. Presumably, the ground fabric of the pressure-sensitive adhesive tape for a joint portion of Example 1 which has as a support a high twist fabric has an uneven surface on the back side thereof and when the wrapped end portion of the tape is attached to another tape, it is attached to this uneven back side and in addition when the whole pressure-sensitive adhesive tape is wetted with water, the high twist fabric itself absorbs water, with the result that the water resistant self-back adhesion power is considerably reduced. Therefore, in the case of a use mode where it is attached in a wrapped state, the pressure-sensitive adhesive tape tends to come to be peeled off at the wrapped portion.

On the other hand, the pressure-sensitive adhesive tape for a joint portion of Example 13, which has as a support a knitted fabric capable of stretching and contracting in transverse and longitudinal directions that is laminated with an ultrathin polyurethane film, so that in its use mode, the polyurethane side is exposed. Therefore, the support has a waterproofing property and causes no reduction in adhesive power, so that the pressure-sensitive adhesive tape exhibits good water resistant self-back adhesion power and in a practical use mode, it showed excellent results in evaluation of water-resistant adhesion.

Effects of the Invention

As described above, the present invention provides a pressure-sensitive adhesive tape for a joint portion that is provided with a non-adherent or weakly adherent portion at a specified position and with a cut line to enable users to easily and simply perform the attachment of a pressure-sensitive adhesive tape for taping, which has been conventionally difficult to do and a method of using such a pressure-sensitive adhesive tape for a joint portion. The non-adherent or weakly adherent portion of the pressure-sensitive adhesive tape of the present invention not only is useful for identifying the site at which the tape is to be applied but also prevents the site from giving a sense of incompatibility or getting stuffy, thus giving more comfortable feeling upon attachment. Further, use of a high twist fabric having a specified elongation as the support gives rise to good fixability with respect to the target joint portion, so that the pressure-sensitive adhesive tape of the present invention is also excellent in the effect of alleviating a pain on the target site. The pressure-sensitive adhesive tape having a specified size for fixing a knee joint exhibits particularly excellent effects in ease of application and alleviation of a pain on the target site since it has a proper size for fixing a knee joint.

Provision, if any, of a tab portion of a semi-circular or the like shape at the end portion of the pressure-sensitive adhesive tapes separated by a cut line increases visibility and handleability of the overlapped end portions of pressure-sensitive adhesive tape and at the same time can prevent coming off of one the overlapped end portions from the other.

Further, use of a high twist fabric having a specified elongation and strength provides good fixability with respect to the target knee joint portion so that the resultant pressure-sensitive adhesive tape is also excellent in the effect of alleviating a pain on the target site.

Also, in the case where the support has been subjected to water repellent treatment or has laminated thereon an ultrathin polyurethane film on the self-back, the resultant pressure-sensitive adhesive tape is difficult to come off when wetted with water or much perspiration occurs upon practicing exercise, since for example, an ultrathin polyurethane film-laminated knitted fabric has a waterproofing property, and also has good kickback and fixability, so that the pressure-sensitive adhesive tape of the present invention exhibits excellent pain-alleviating effect.

The present invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A pressure-sensitive adhesive tape for providing support to a joint of a body, said joint having an inner portion on which the joint closes and oppositely disposed outer portion, comprising a support with first and second support portions, said support having a longer side and a shorter side and a pressure-sensitive adhesive layer on one side of the support in at least a portion thereof,
    wherein the tape is provided with a substantially non-adherent portion sized for positioning on said joint inner portion, and
    wherein the tape at each of said first and second support portions has a single cut forming two tape portions with no space between the tape portions extending from an end of the shorter side to near the substantially non-adherent portion and is sized to close over said joint outer portion.

2. A pressure-sensitive adhesive tape for providing support to a joint portion as claimed in claim 1, wherein the substantially non-adherent portion comprises a non-adherent member and wherein the first and second support portions each having a pressure-sensitive adhesive on one side thereof and are coupled through the substantially non-adherent member, forming a rectangular shape having longer sides and shorter sides.

3. A pressure-sensitive adhesive tape for providing support to a joint portion as claimed in claims 2, wherein the support has a tensile strength of 10 N/19 mm-width or more and a 20% modulus of 0.5 to 8 N/19 mm-width.

4. A pressure-sensitive adhesive tape for providing support to a joint portion as claimed in claim 1, wherein the tape comprises a rectangular support having longer sides and shorter sides having a pressure-sensitive adhesive tape layer over entire surface of one side thereof, and a non-adherent portion comprising a non-adherent member laminated on the pressure-sensitive adhesive tape layer.

5. A pressure-sensitive adhesive tape for providing support to a joint portion as claimed in claims 4, wherein the support has a tensile strength of 10 N/19 mm-width or more and a 20% modulus of 0.5 to 8 N/19 mm-width.

6. A pressure-sensitive adhesive tape for providing support to a joint portion as claimed in claim 1, wherein the tape comprises a rectangular support having longer sides and shorter sides with a pressure-sensitive adhesive tape layer over surface of one side thereof, and a substantially non-adherent portion where pressure-sensitive adhesive is partially provided on the side of the pressure-sensitive adhesive tape layer.

7. A pressure-sensitive adhesive tape for providing support to a joint portion as claimed in claim 6, wherein the support has a tensile strength of 10 N/19 mm-width or more and a 20% modulus of 0.5 to 8 N/19 mm-width.

8. A pressure-sensitive adhesive tape for providing support to a joint portion as claimed in claim 1, wherein the tape has an elongation of 30% or more in a longitudinal direction.

9. A pressure-sensitive adhesive tape for providing support to a joint portion as claimed in claim 1, wherein the tape has one cut of a length extending from a central portion of the shorter side to the substantially non-adherent portion.

10. A pressure-sensitive adhesive tape for providing support to a joint portion as claimed in claim 1, wherein the tape has a tab portion having a predetermined configuration on a top of a portion of pressure-sensitive adhesive tape separated by the cut.

11. A pressure-sensitive adhesive tape for providing support to a joint portion as claimed in claim 1, wherein the support has a tensile strength of 10 N/19 mm-width or more and a 20% modulus of 0.5 to 8 N/19 mm-width.

12. A pressure-sensitive adhesive tape for providing support to a joint portion as claimed in claim 1, wherein the support comprises a high twist fabric or a knitted fabric having elasticity in two dimensions, the knitted fabric being laminated on one side thereof with a polyurethane film having waterproofing property and permeability.

13. A pressure-sensitive adhesive tape for providing support to a joint portion, comprising a support with first and second support portions, said support having a longer side and a shorter side and a pressure-sensitive adhesive layer on one side of the support in at least a portion thereof, wherein the tape is provided with a non-adherent portion or a substantially non-adherent portion, and wherein the tape at each of said first second support portions has a single cut forming two tape portions with no space between the portions, extending from an end of the shorter side to near the non-adherent or substantially non-adherent portion wherein the support comprises a high twist fabric or a knitted fabric having elasticity in two dimensions, the knitted fabric being laminated on one side thereof with a polyurethane film having waterproofing property and permeability, and wherein the polyurethane film is within a range of about 5 to 30 µm.

14. A pressure-sensitive adhesive tape for providing support to a joint portion as claimed in claim 1, wherein the support comprises a high twist fabric or a knitted fabric having elasticity in two dimensions, one side of the high twist fabric or knitted fabric being subjected to water repellent treatment.

15. A pressure-sensitive adhesive tape for providing support to a joint portion as claimed in claim 1, wherein the substantially non-adherent member comprises one member selected from the group consisting of woven fabric, non-woven fabric, knitted fabric, paper, and plastic sheet.

16. A pressure-sensitive adhesive tape for providing support to a joint portion as claimed in claim 1, wherein the tape is for application to a knee joint.

17. A pressure-sensitive adhesive tape for providing support to a joint portion, comprising a support with first and second support portions, said support having a longer side and a shorter side and a pressure-sensitive adhesive layer on one side of the support in at least a portion thereof, wherein the tape is provided with a non-adherent portion or a substantially non-adherent portion, and wherein the tape at each of said first second support portions has a single cut forming two tape portions with no space between the tape portions, extending from an end of the shorter side to near the non-adherent or substantially non-adherent portion, wherein the tape is for application to a knee joint, and wherein the shorter side has a length of 5 to 15 cm and the longer side as a length of 35 to 55 cm.

18. A method of using a pressure-sensitive adhesive tape for providing support to a joint of a body, said joint having an inner portion on which the joint closes and an oppositely disposed outer portion, which comprises a support having a longer side and a shorter side and a pressure-sensitive adhesive layer on one side of the support in at least a portion thereof, wherein the tape is provided with a non-adherent portion or a substantially non-adherent portion, and wherein the tape has a single cut forming two tape portions with no space between the tape portions, extending from an end of the shorter side to near the non-adherent or substantially non-adherent portion, the method comprising:

applying the non-adherent or substantially non-adherent portion of the pressure-sensitive adhesive tape for fixing a joint to an inner portion of a the joint, separating the tape along the cut, and winding the separated tape portions around said outer portion of the joint to provide support to the joint.

19. A method of using a pressure-sensitive adhesive tape for providing support to a joint portion as claimed in claim 18, wherein the applying step is performed with respect to a non-adherent member, and wherein the winding step is performed with respect to a tape that comprises two supports each having a pressure-sensitive adhesive on one side thereof coupled through the non-adherent member, and forming a rectangular shape having longer sides and shorter side.

* * * * *